United States Patent
Padovan et al.

(10) Patent No.: US 10,836,778 B2
(45) Date of Patent: Nov. 17, 2020

(54) PROCESS FOR THE PREPARATION OF CYCLOPROPYLDIKETOPIPERAZINES AND OF A KEY INTERMEDIATE OF DS-5272

(71) Applicant: F.I.S.—Fabbrica Italiana Sintetici S.p.A., Montecchio Maggiore (IT)

(72) Inventors: Pierluigi Padovan, Montecchio Maggiore (IT); Kexia Lou, Zhejiang (CN)

(73) Assignee: F.I.S.—FABBRICA ITALIANA SINTETICI S.P.A., Montecchio Maggiore (IT)

( * ) Notice: Subject to any disclaimer, the term of this patent is extended or adjusted under 35 U.S.C. 154(b) by 0 days.

(21) Appl. No.: 16/481,628

(22) PCT Filed: Jan. 15, 2018

(86) PCT No.: PCT/EP2018/050838
§ 371 (c)(1),
(2) Date: Jul. 29, 2019

(87) PCT Pub. No.: WO2018/145860
PCT Pub. Date: Aug. 16, 2018

(65) Prior Publication Data
US 2019/0389881 A1    Dec. 26, 2019

(30) Foreign Application Priority Data
Feb. 13, 2017    (EP) .................................... 17155811

(51) Int. Cl.
*C07D 513/04* (2006.01)
*C07D 241/38* (2006.01)

(52) U.S. Cl.
CPC ......... *C07D 513/04* (2013.01); *C07D 241/38* (2013.01)

(58) Field of Classification Search
CPC .................................................. C07D 513/04
See application file for complete search history.

(56) References Cited

FOREIGN PATENT DOCUMENTS

| EP | 2336132 A1 | 6/2011 |
|---|---|---|
| EP | 2380892 A1 | 10/2011 |
| WO | 2015095227 A2 | 6/2015 |

OTHER PUBLICATIONS

Soldevilla et al., "The N-Cyclopropylimine-1-pyrroline Photorearrangement as a Synthetic Tool: Scope and Limitations", The Journal of Organic Chemistry, 2005, vol. 70, No. 17, pp. 6976-6979.

Miyazaki et al., "Discovery of DS-5272 as a promising candidate: A potent and orally active p53-MDM2 interaction inhibitor", Bioorganic & Medicinal Chemistry, 2015, vol. 23, No. 10, pp. 2360-2367.

International Search Report and Written Opinion for Corresponding International Application No. PCT/EP2018/050838 (15 Pages) (dated Jun. 19, 2018).

*Primary Examiner* — Paul V Ward
(74) *Attorney, Agent, or Firm* — Lucas & Mercanti, LLP

(57) ABSTRACT

Object of the present invention is an improved process for the preparation of cyclopropyldiketopiperazines and thereof key intermediates.

11 Claims, No Drawings

PROCESS FOR THE PREPARATION OF CYCLOPROPYLDIKETOPIPERAZINES AND OF A KEY INTERMEDIATE OF DS-5272

CROSS-REFERENCE TO RELATED APPLICATIONS

This application is a 371 of PCT/EP2018/050838, filed Jan. 15, 2018, which claims the benefit of European Patent Application No. 17155811.7, filed Feb. 13, 2017.

TECHNICAL FIELD

The present invention refers to process for the preparation of cyclopropyldiketopiperazines, which also are key intermediates for the synthesis of compound having anti-tumor activity, in particular of the compound named DS-5272.

BACKGROUND ART

The present invention relates to a convenient process for the preparation of cyclopropyldiketopiperazines, one of them being a key intermediate for the synthesis of a potent and orally active p53-MDMS interaction inhibitor. In particular, for example, the compound named DS-5272 or ((5R,6S)-5-(4-chloro-3-fluorophenyl)-6-(6-chloropyridin-3-yl)-3-isopropyl-6-methyl-5,6-dihydroimidazo[2,1-b]thiazol-2-yl)((2S,4R)-2-((R)-6-ethyl-4,7-diazaspiro[2.5]octane-7-carbonyl)-4-fluoropyrrolidin-1-yl)methanone, having the following structure:

(IX)

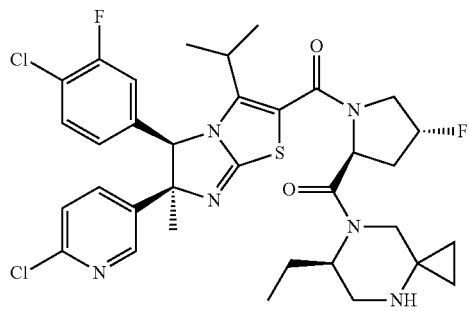

is an active pharmaceutical ingredient which acts as a potent inhibitor of p53-MDM2, therefore, useful to treat cancer.

The patent publication EP2380892A, discloses a class of MDM2 inhibitor, which are potent inhibitors of p53-MDM2 therefore useful for the treatment of human cancer. In particular the selected active compound ((5R,6S)-5-(4-chloro-3-fluorophenyl)-6-(6-chloropyridin-3-yl)-3-isopropyl-6-methyl-5,6-dihydroimidazo[2,1-b]thiazol-2-yl)((2S,4R)-2-((R)-6-ethyl-4,7-diazaspiro [2.5]octane-7-carbonyl)-4-fluoropyrrolidin-1-yl)methanone is prepared, in example 5, by coupling of the intermediate 1 named (5R,6S)-5-(4-chloro-3-fluorophenyl)-6-(6-chloropyridin-3-yl)-6-methyl-3-(propan-2-yl)-5,6-dihydroimidazo[2,1-b][1,3]thiazole-2-carboxylic acid and having the following structure:

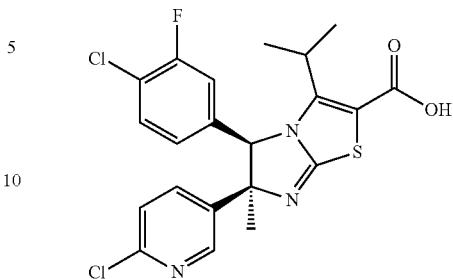

Intermediate 1 with the Intermediate 2 named 1-{(6R)-6-ethyl-7-[(2S,4R)-4-fluoropyrrolidine-2-carbonyl]-4,7-diazaspiro[2.5]octan-4-yl}-2,2,2-trifluoroethan-1-one and having structure:

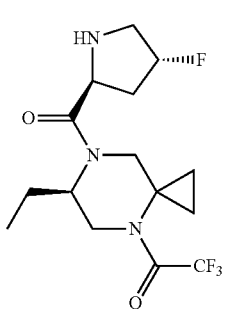

Intermediate 2 followed by the removal of the COCF$_3$ protecting group.

The preparation of the Intermediate 2 is also disclosed in details in the example 10 and 11 of the same patent publication, as a synthetic method involving six steps of synthesis, starting from methyl (2R)-2-(benzylamino)butanoate, according to the following schema:

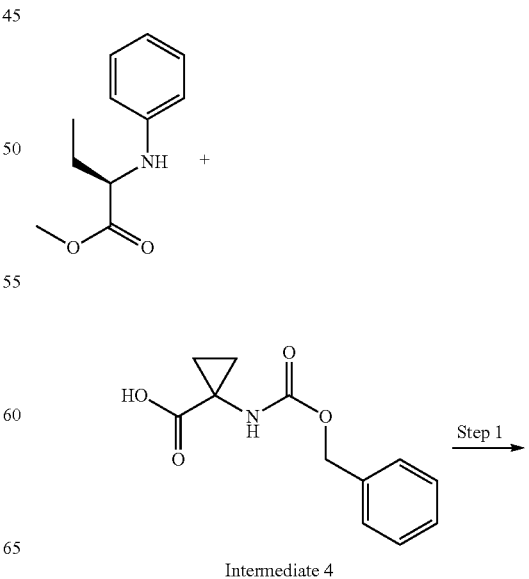

Intermediate 4

-continued

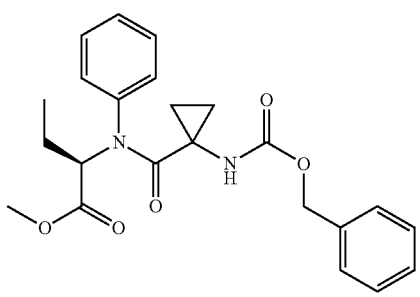

Step 2

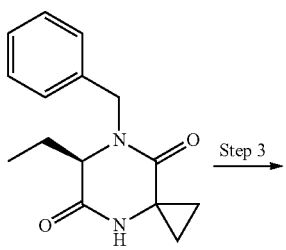

Intermediate 3

Step 3

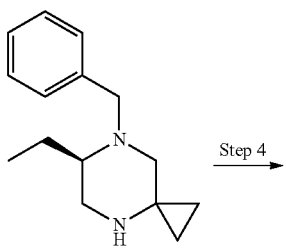

Step 4

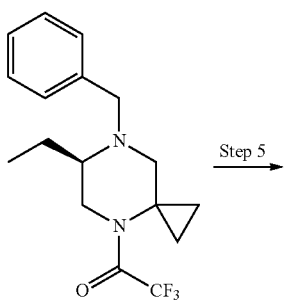

Step 5

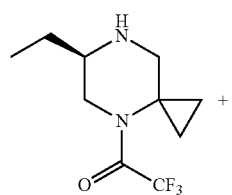

+

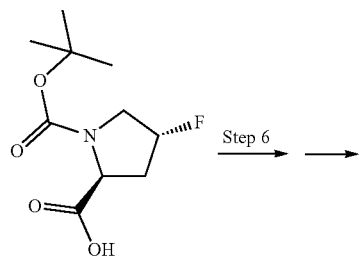

Step 6

-continued

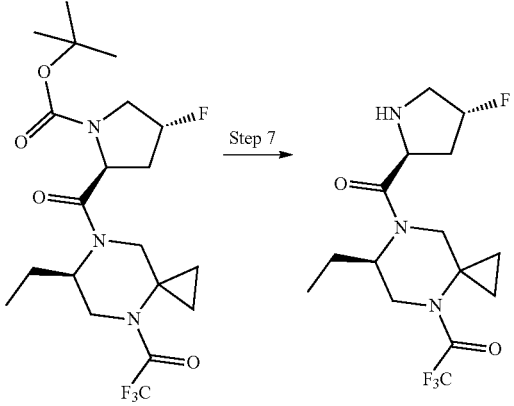

Step 7

Intermediate 2

According to said publication, the key Intermediate 3, named (6R)-7-benzyl-6-ethyl-4,7-diazaspiro[2.5]octane-5,8-dione and having the following structure:

Intermediate 3

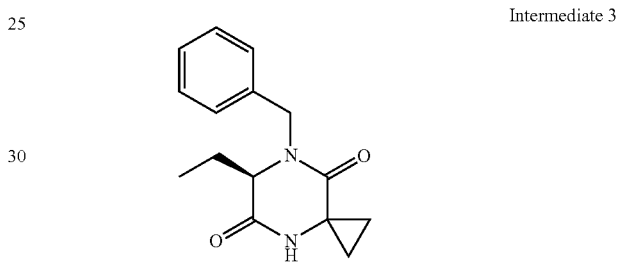

is prepared in two steps from the compound named methyl (2R)-2-(benzylamino)butanoate, and having the following structure:

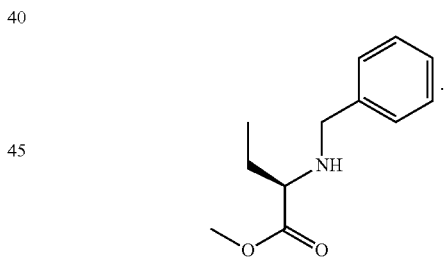

The same procedure is disclosed in another patent publication, i.e. EP2336132A, wherein it is disclosed the synthesis of the compound named 7-benzyl-4,7-diazaspiro[2.5]octane-5,8-dione of formula:

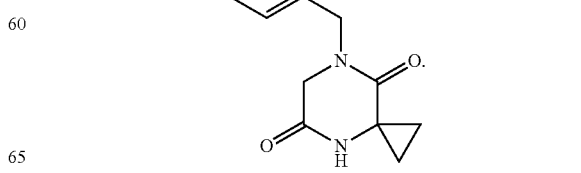

Said prior art methods for the preparation of (6R)-7-benzyl-6-ethyl-4,7-diazaspiro[2.5]octane-5,8-dione of formula:

Intermediate 3

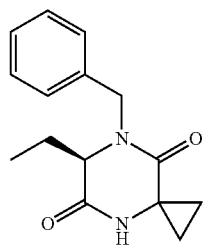

require many synthetic steps, the use of starting materials quite expensive such as 1-{[(benzyloxy)carbonyl]amino}cyclopropane-1-carboxylic acid or methyl (2R)-2-anilinobutanoate, or their preparation.

Moreover, said prior art methods require the use of hydrogen atmospheres for carried out the cyclisation reaction of step 2, i.e. reduction reaction. The use of hydrogen atmospheres required particular reactors capable of withstanding high pressure, i.e. autoclaves.

Furthermore, the use of hydrogen could by very dangerous as it is able to generate explosive mixtures with oxygen.

Moreover, it is noted that the compound 1-{[(benzyloxy)carbonyl]amino}cyclopropane-1-carboxylic acid, having the following structure:

Intermediate 4

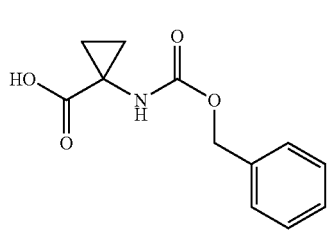

is the key intermediate for the synthesis of the intermediate 3.

A process for the preparation of the key Intermediate 4 is also disclosed in WO 2015/095227A2, wherein sais compound is prepared from the compound named 1-aminocyclopropane-1-carboxylic acid, having the following structure:

Intermediate 5

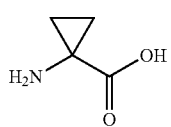

The preparation of the Intermediate 5 is also disclosed in details in Synthetic communications 22(20) 1992, as a synthetic method involving four steps of synthesis, starting from methyl 2-diphenylmethyleneaminoacrylate.

The compound named ethyl 1-[(diphenylmethylidene)amino]cyclopropane-1-carboxylate having the following structure:

(V-a)

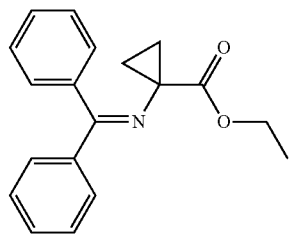

and its preparation is disclosed in details in the *J. Org. Chem.* 2005, 70, 6976-6979, as a synthetic method involving one step of synthesis, starting from Benzophenoneimine and 1-ethoxycarbonylcyclopropanamine.

SUMMARY OF INVENTION

The problem addressed by the present invention is therefore that of providing an improved process for the preparation of 7-benzyl-4,7-diazaspiro[2.5]octane-5,8-dione and analogues thereof which allows to get round to the drawbacks above reported with reference to the known prior art.

In particular, such improved process should also allow to avoid the use of special and expensive apparatus for carry out the reduction reaction, i.e. the use of autoclaves.

Moreover, such improved process should also allow to avoid the use of hydrogen atmospheres for carried out the process for preparation of 7-benzyl-4,7-diazaspiro [2.5]octane-5,8-dione and analogues thereof.

This problem is solved by a process for the preparation of a said compound, which also is a key intermediate for the synthesis of compounds having anti-tumor activity, as outlined in the annexed claims, whose definitions and combinations are integral part of the present description.

Further features and advantages of the process according to the invention will result from the description hereafter reported of examples of realization of the invention, provided as an indication and not as a limitation of the invention.

DESCRIPTION OF EMBODIMENTS

Object of the present invention is a process for the preparation of the compound of formula (I) or R or S optical isomer thereof:

(I)

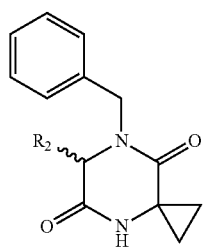

wherein $R_2$ is hydrogen, methyl or ethyl, comprising the following steps:
(a) reaction of the compound of formula (III):

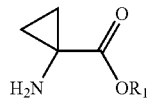

wherein $R_1$ is 01-4 linear or branched alkyl, with a compound of formula (IV):

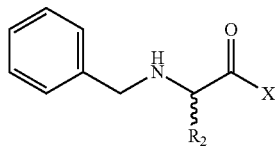

wherein $R_2$ is hydrogen, methyl or ethyl, and wherein X is chosen between hydroxyl, halogen or other leaving group; for providing the compound of formula (II) or salt thereof:

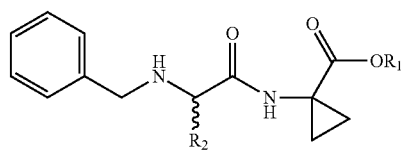

wherein $R_2$ is hydrogen, methyl or ethyl, and wherein $R_1$ is $C_{1-4}$ linear or branched alkyl;
(b) cyclization of the compound of formula (II) obtained in step (a) to the compound of formula (I):

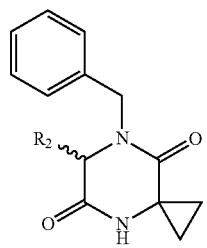

wherein $R_2$ is hydrogen, methyl or ethyl.

The compound of formula (I) comprises either the single R enantiomer, or the S enantiomer, or the racemic mixture or their mixtures in any R/S ratio.

The compound of formula (I) having R configuration is a preferred compound.

The configurations above described always refers to the configuration of the carbon bonded to the $R_2$ group.

The term of linear or branched $C_{1-4}$ alkyl thus means an alkyl group selected among: methyl, ethyl, n-propyl, isopropyl, n-butyl, isobutyl, sec-butyl and tert-butyl. Thus, in the compound of formula (III) and compound of formula (II), $R_1$ has said meaning.

The compound of formula (III) can be in the form of free base or as a salt. Examples of salts of the compound (III) are those having halides as counter ions, hence, the salt formed with hydrochloric acid or hybrobromic acid (i.e. compound (III) hydrochloride or hydrobromide).

The compound of formula (II) and compound (IV) can be in the form of free base or as a salt. Examples of salts of the compound (II) and (IV) can be those having halides as counter ions, hence, the salt formed with hydrochloric acid or hybrobromic acid (i.e. compound (II) hydrochloride or hydrobromide).

The step (a) of the process of the present invention is carried out with a compound of formula (IV) or salts thereof:

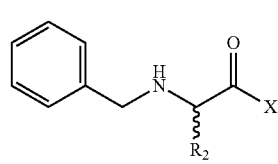

wherein X is chosen between hydroxyl, halogen or any group capable to activate the carboxyl function.

In the compound of formula (IV) halogen is fluorine, chlorine, bromine or iodine.

In the compound of formula (IV), the group capable to activate the carboxyl function is therefore a group selected among the group comprising azides, substituted hydroxylamines (formed, for example, with N-hydroxysuccinimide, 1-hydroxy-benzotriazole), fluoralcoholate esters (formed, for example, with trifluoroethanol), anhydrides (formed, for example, with pivaloyl chloride, ethyl chloroformate, etc.), esters with phenols (also replaced by electron-attractor groups, for example 2-hydroxypyridine), labile amides (formed, for example, with imidazole, triazines, etc.).

According to a preferred embodiment, in the compound of formula (IV) X is chlorine.

The step a) of the process of the present invention is carried out in presence of one or more basis.

In particular, the process is carried out in presence of an inorganic or an organic base or a mixture of these.

According to a preferred embodiment, the step a) of the process according to the invention can be carried out in the presence of a base such as an inorganic base.

The inorganic base that can be used to carry out the step a) of process of the present invention can be chosen among, for example, acetates, bicarbonates, carbonates, hydroxides, phosphates, alcoholates of alkaline or alkaline-heart metals.

Said inorganic base can also be sodium hydroxide, sodium carbonate, sodium bicarbonate, potassium hydroxide, potassium carbonate, potassium bicarbonate, caesium hydroxide, caesium carbonate, lithium hydroxide, lithium carbonate, potassium dihydrogen phosphate, potassium hydrogen phosphate, potassium phosphate, sodium dihydrogen phosphate, sodium hydrogen phosphate or sodium phosphate.

The step a) of process according to the invention can be carried out in the presence of an organic base such as for example an organic amine of general formula $NR_3$ with R being linear or branched $C_{1-7}$ alkyl and wherein the three R groups can be the same or different. The amine can also be selected among pyrrolidine, N-alkyl substituted pirrolydine, piperidine, morpholine, N-alkyl substituted piperidine and N-alkyl substituted morpholine. Suitable bases are, for instance, N-Methylmorpholine, Triethylamine, diazabicyclooctane (DABCO), Ethyldiisoproprilamine and TMEDA (Tetramethylethylendiamine). The Triethylamine is preferred since it provides higher molar yields.

The step a) of the process according to the invention can be carried out in the presence of one or more organic solvents such as, for example, toluene, xylene, halogenated solvents, dichloromethane (abbreviated DCM), dimethylformamide (DMF), N-methylporrolidone (NMP), dimethylsolphoxide (DMSO), tetrahydrofuran (THF), dioxane, methyl-t-butyl ether (MTBE), diethyl ether. Preferably the reaction is carried out in aromatic solvent or an ether solvent such as toluene, xylene, MTBE, DCM, dioxane, methyl-tetrahydrofuran (Me-THF), THF, being more preferred THF and DCM.

The step a) is carried out in an organic solvent, preferably in THF or Me-THF or DCM or toluene mixtures thereof.

The step a) wherein in the compound of formula (IV), X is chlorine can be conveniently carried out in a solvent being DCM or THF or toluene.

The step a) wherein in the compound of formula (IV), X is chlorine can be conveniently carried out in DCM and trimethylamine, as base.

The step a) can also be carried out with the compound of formula (IV) wherein X is OH, using, for example, a condensing agent such as a carbodiimide, like, for example, dicyclohexylcarbodiimide, or by means of propylphosphonic anhydride (T3P), 2-2-chloro methylpyridinium iodide, cyanuric chloride, 2-chloro-4,6-dimethoxy-1,3,5-triazine and phosphonium, uronium and guanidinium salts, etc.

The step b) of the process of the present invention can be carried out by thermal cyclization reaction of the compound of formula (II).

The step b) according can be carried out teachings of the skilled person regarding the synthesis of 2,5-dioxopiperazine by cyclization of dipeptides.

The step b) is carried out in an organic solvent, preferably in $C_{3-5}$ alcohol or hydrocarbon solvent. Hydrocarbon solvent are, e.g. toluene, xylene, chlorobenzene, tetralyne, heptane, said solvents can also be used for carrying out the step b). More preferably are suitable solvents to carry out the step b) aromatic hydrocarbon solvent or $C_4$ alcohol, again more preferably toluene, xylene or n-butanol.

The product of formula (I) wherein $R_2$ is hydrogen obtained in the step b) can be purified by slurry with water or water containing from 0.01 to 0.1% w/w of aqueous hydrochloric acid.

Alternatively or additionally, the product of formula (I) wherein $R_2$ is hydrogen obtained at the step b) can be purified by crystallization or recrystallization with acetonitrile or acetonitrile containing from 0.1 to 2% w/w of acetic acid, preferably 0.5% w/w. The percentage % w/w is referred to the weight of acetic acid compared to the weight of acetonitrile.

The crystallization or recrystallization of compound of formula (I) ca be carried out using from 5 to 15 volumes (V) of acetonitrile (ACN) or ACN containing from 0.1 to 2% w/w of acetic acid, preferably 9 volumes (V).

The step b) is carried out at temperature comprised between 60° C. and 130° C., preferably between 80° C. and 110° C. or at reflux temperature of n-butanol (118° C.).

The compound of formula (I) wherein $R_2$ is hydrogen, prepared according to the invention, has a chemical purity higher than 99.80 HPLC A/A % as determined by the method HPLC of example 16.

According to a more preferred embodiment of the process, the compound of formula (I) wherein $R_2$ is hydrogen has chemical purity higher than 99.80 HPLC A/A % and each single impurity not more than 0.07%.

The compound of formula (I) wherein $R_2$ is hydrogen, prepared according to the invention, has a chemical purity higher than 99.80 GC A/A % as determined by the GC method of example 24.

According to a more preferred embodiment of the process, the compound of formula (I) wherein $R_2$ is hydrogen has chemical purity higher than 99.80 GC A/A % and each single impurity not more than 0.04%.

Moreover, the process according to the present invention could also involve previous steps for the preparation of the compound of formula (III):

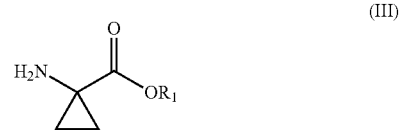

wherein $R_1$ is $C_{1-4}$ linear or branched alkyl, said previous steps being the following steps:

a-1) reaction of the compound of formula (VI):

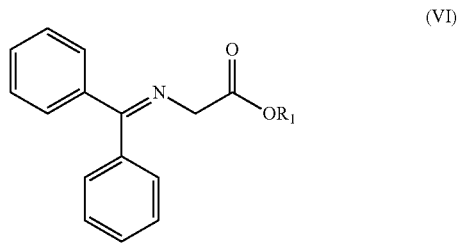

wherein $R_1$ is $C_{1-4}$ linear or branched alkyl, with a compound of formula (VII):

wherein $X_1$ and $X_2$ are independently an halogen, mesilate, tosilate, besilate, or triflate group;

to give the compound of formula (V):

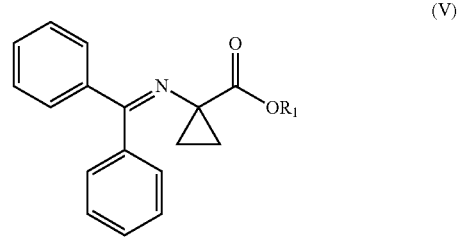

wherein $R_1$ is $C_{1-4}$ linear or branched alkyl;

b-1) deprotaction of the compound of formula (V):

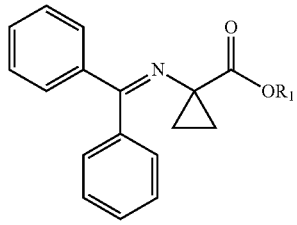

(V)

obtained in step a-1) to give the compound of formula (III):

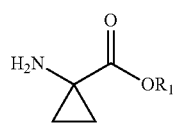

(III)

wherein $R_1$ is $C_{1-4}$ linear or branched alkyl.

The step a-1) of the process of the present invention is carried out with a compound of formula (VII):

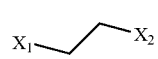

(VII)

wherein $X_1$ and $X_2$ are independently an halogen, mesilate, tosilate, besilate or triflate.

The halogen of $X_1$ and $X_2$ means chorine, fluorine, iodine or bromine.

According to a preferred embodiment of the process, the compound of formula (VII) is the one in which $X_1$ and $X_2$ are both chlorine, bromine or iodine.

According to a more preferred embodiment of the process, the compound of formula (VII) is the one in which X1 and X2 are both bromine, since it provides higher molar yields.

According to a preferred embodiment, the step a-1) of the process is carried out using from 2.5 to 3.5 molar equivalents of the compound of formula (VII) in which X1 and X2 are both bromine, referenced to the compound of formula (VI), more preferably about 3.0 molar equivalents since it provides higher molar yields of the compound of formula (V).

The step a-1) of the process of the present invention is carried out in presence of one or more basis.

In particular, the step a-1) of the process is carried out in presence of an inorganic or an organic base or a mixture of these.

According to a preferred embodiment, the step a-1) of the process according to the invention can be carried out in the presence of a base such as an inorganic base.

The inorganic bases used to carry out the step a-1) of process of the present invention can be chosen among, for example, acetates, bicarbonates, carbonates, hydroxides, phosphates, alcoholates or hydrides of alkaline or alkaline-heart metals.

Said inorganic base can also be sodium hydroxide, sodium hydride, sodium carbonate, sodium bicarbonate, potassium hydroxide, potassium carbonate, potassium bicarbonate, caesium hydroxide, caesium carbonate, lithium hydroxide, lithium carbonate, potassium dihydrogen phosphate, potassium hydrogen phosphate, potassium phosphate, sodium dihydrogen phosphate, sodium hydrogen phosphate, sodium phosphate. The sodium hydride, potassium hydroxide, potassium carbonate and cesium carbonate are preferred since it provides higher molar yields.

According to a more preferably embodiment, the step a-1) of the process according to the invention can be carried out in the presence of sodium hydride or sodium hydride 60% on mineral oil or potassium hydroxide.

The process according to the invention can be carried out in the presence of an organic base such as, for example, an organic amine of general formula $NR_3$ with R being linear or branched $C_{1-7}$ alkyl and wherein the three R groups can be the same or different. The amine can also be selected among pyrrolidine, N-alkyl substituted pirrolydine, piperidine, morpholine, N-alkyl substituted piperidine and N-alkyl substituted morpholine. Suitable bases are for instance N-Methlylmorpholine, Triethylamine, DABCO, Ethyldiisoproprilamine and TMEDA (Tetramethylethylendiamine). The Triethylamine is preferred since it provides higher molar yields.

The step a-1) of the process of the present invention can be optionally carried out in presence of a phase transfer catalyst.

Said phase transfer catalyst can be, for example, an organic ammonium salt of general formula $NR_4X$ wherein X is hydroxyl or halogen and R is linear or branched $C_{1-12}$ alkyl, aryl or substituted aryl, and the four R groups can be the same or different. The triethylbenzilamminium chloride is preferred since it provides higher molar yields.

The step a-1) according to the invention can be carried out in the presence of one or more solvents such as e.g. toluene, xylene, DMF, NMP, DMSO, THF, Dioxane, MTBE, diethyl ether.

Preferably the reaction of step a-1) is carried out in an aromatic solvent or an ether solvent such as, for example, toluene, xylene, methyl-t-butyl ether (MTBE), Dioxane, methyl-THF, tetrahydrofuran (THF).

According to a more preferably embodiment, the step a-1) of the process according to the invention is carried out in an aromatic solvent.

According to an again more preferably embodiment, the step a-1) of the process according to the invention, is carried out in an hydrocarbon aromatic solvent.

According to a more preferably embodiment, the step a-1) of the process according to the invention is carried out in toluene or xylene.

The step a-1) according to the invention can be carried out in the presence of sodium hydride or sodium hydride 60% on mineral oil one in an aromatic solvent, preferably, in an hydrocarbon aromatic solvent.

The step a-1) according to the invention can be carried out in the presence of sodium hydride or sodium hydride 60% on mineral oil one in toluene.

According to a preferred embodiment, the step b-1) of the process is carried out using from 2.5 to 3.5 molar equivalents of sodium hydride or sodium hydride 60% in mineral oil, referenced to the compound of formula (VI), more preferably about 3.0 molar equivalents since it provides higher molar yields of the compound of formula (V).

According to a preferred embodiment, the step a-1) of the process according to the invention can be carried out at temperature between 0 to 20° C., more preferably between 5 to 10° C.

The step b-1) according to the invention can be carried out in the presence of acetic acid.

The step b-1) according to the invention can be carried out in the presence of one or more solvents such as toluene, xylene, DMF, NMP, DMSO, Dioxane, MTBE, water, acetic acid, and mixture of water and acetic acid.

The step b-1) according to the invention can also be carried out in the presence of acetic acid in an aromatic solvent such as toluene.

According to a preferable embodiments, the step b-1) of the process of the invention is carried out in a mixture of acetic acid and water.

According to a preferred embodiment, the step b-1) of the process is carried out using from 1 to 2 molar equivalents of acetic acid, referenced to the compound of formula (V), more preferably about 1.65 molar equivalents since it provides higher molar yields of the compound of formula (III).

According to a preferred embodiment, the step b-1) of the process according to the invention can be carried out at temperature between 30 to 80° C., preferably between 40° C. and 60° C., more preferably at 50° C.

The compound of formula (VI), can be prepared according to the following reaction scheme:

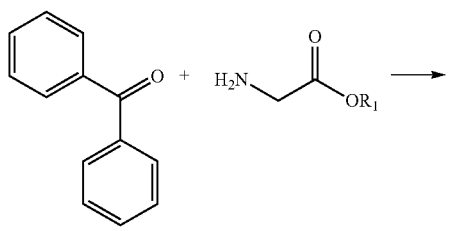

(VI)

The above commercially available compound (VI) can be prepared for example by chemical condensation of glycine ester with benzophenone as described in literature.

The preparation of the compound of formula (VI) can be performed applying the teachings of Synlett, 2016, 27(9), 1403-1407; Journal of the American Chemical Society, 2015, 137(45), 14446-14455; Angewandte Chemie, International Edition, 2013 52(49), 12942-12945; Organic Letters, 2012 14(2), 552-555.

Moreover, the process according to the present invention, can also comprise the further step c) of reduction of the compound, obtained in step b), of formula (I):

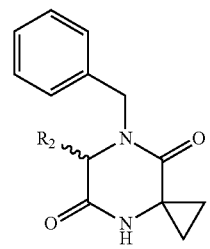

wherein $R_2$ is hydrogen, methyl or ethyl, to give the compound of formula (I-bis):

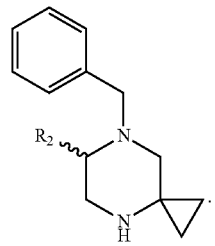

wherein $R_2$ is hydrogen, methyl or ethyl.

Said further reduction step can be carried out applying the teachings of the skilled person regarding the reduction of carbonyl groups. In particular, the reduction can be carried out in presence of $BH_3$/THF complex in THF.

In particular, the reduction in presence of $BH_3$/THF complex in THF can be carried out at 0° C., according to the teaching of EP2380892A, example 3, Step 3, or according to the teaching of Bioorganic & Medicinal Chemistry 23 (2015) 2360-2367.

The following schema 1 summarizes the overall process of the invention:

Schema 1

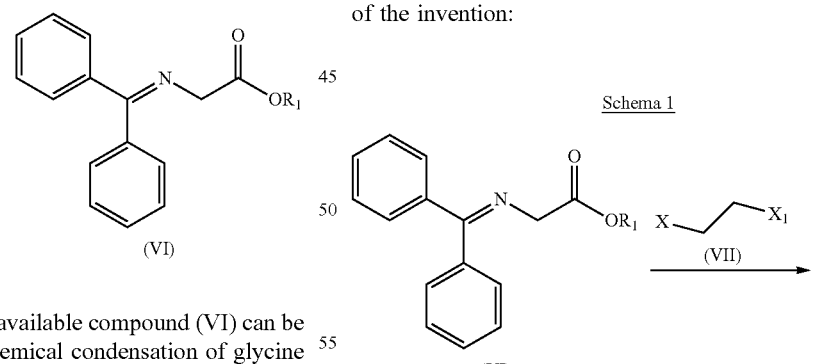

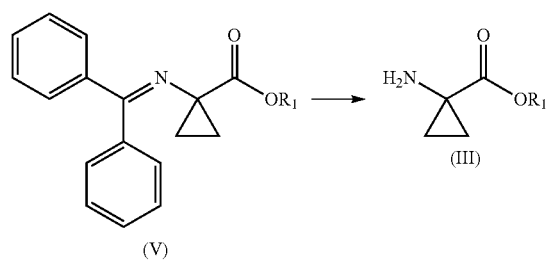

-continued

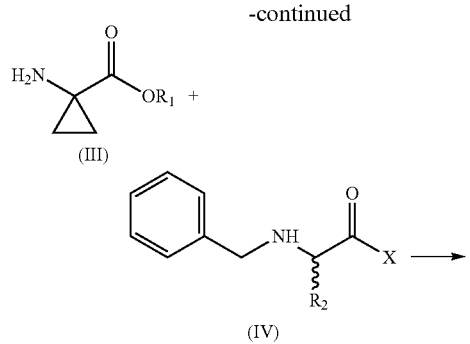

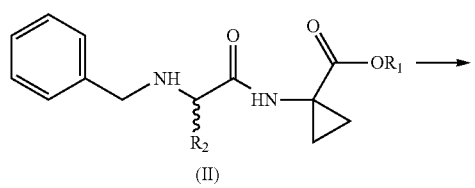

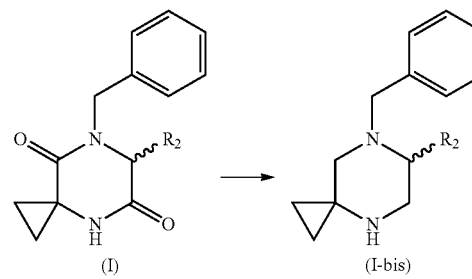

The process of the present invention thus provides new intermediates, i.e. the compound of formula (II):

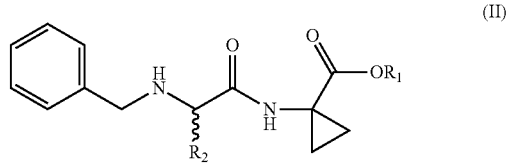

wherein $R_2$ is hydrogen, methyl or ethyl, and wherein $R_1$ is $C_{1-4}$ linear or branched alkyl and the configuration of the stereocenter of $R_2$ is R or S or R/S mixture, or racemate; with the exception of the compound of formula (II) wherein $R_2$ is hydrogen and $R_1$ is methyl.

According to a preferred embodiment, the compound of formula (II):

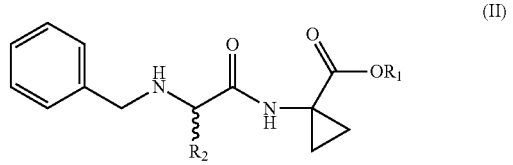

has the following formula:

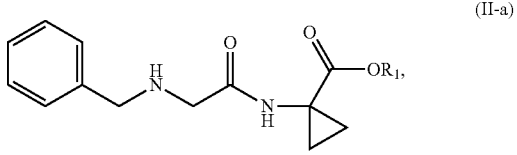

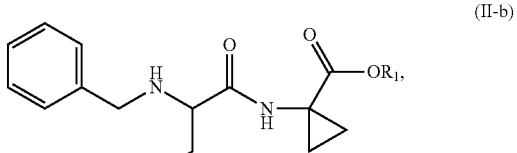

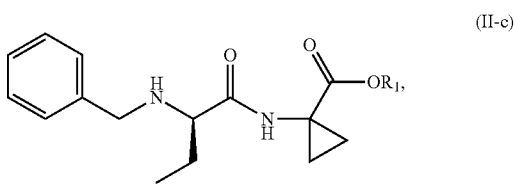

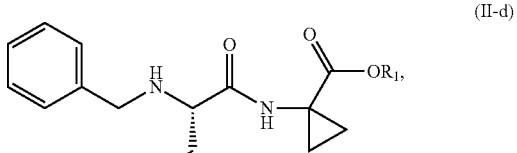

wherein $R_1$ is $C_{1-4}$ linear or branched alkyl.

The process of the present invention thus also provides new intermediates, i.e. the compound of formula (V):

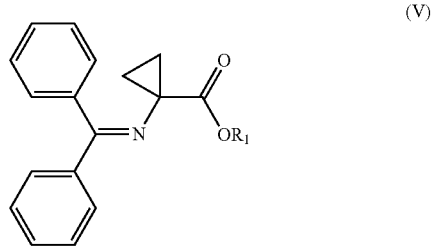

wherein $R_1$ is $C_{3-4}$ linear or branched alkyl.

The compound of formula (II), (III), (V), (X):

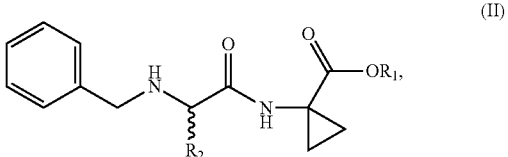

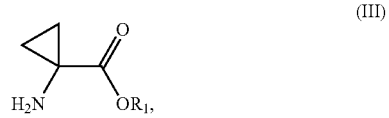

(V)

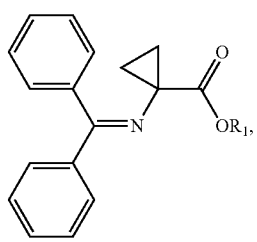

(X)

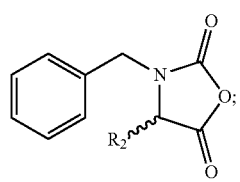

wherein in the compound of formula (II) and (X) $R_2$ is hydrogen, methyl or ethyl, and wherein in each of the compounds $R_1$ is $C_{1-4}$ linear or branched alkyl; with the exception of the compounds:

of formula (II) wherein $R_2$ is hydrogen and $R_1$ is methyl;

of formula (III) wherein $R_1$ is methyl;

can be used for the preparations of compound of formula (I) or R or S optical isomer, and the compound of formula (I-bis) or R or S optical isomer, or salt thereof:

(I)

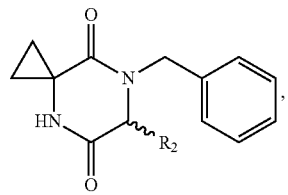

(I-bis)

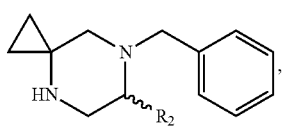

wherein $R_2$ in compound (I) and (I-bis) is hydrogen, methyl or ethyl.

According to a preferred embodiment, the following compound of formula (II-a), (II-b), (II-c), (II-d), (III-a), (V-a), (X-a), (X-b), (X-d):

(II-a)

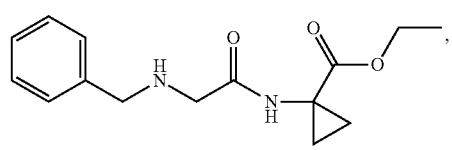

(II-b)

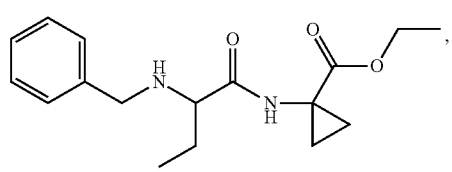

(II-c)

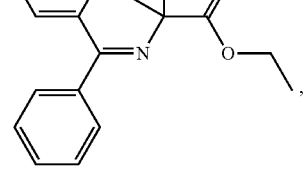

(II-d)

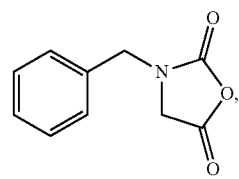

(III-a)

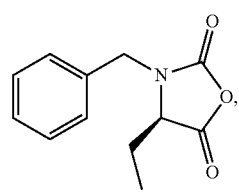

(V-a)

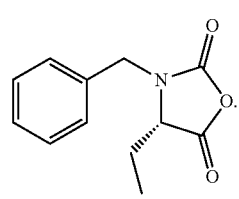

(X-a)

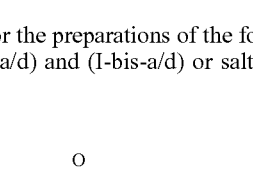

(X-b)

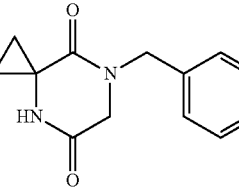

(X-d)

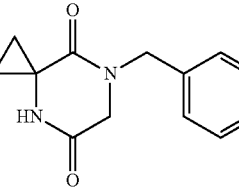

can be used for the preparations of the following compound of formula (I-a/d) and (I-bis-a/d) or salt thereof:

(I-a)

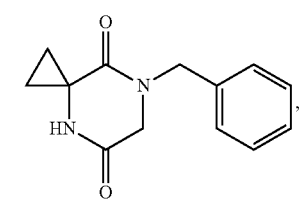

-continued

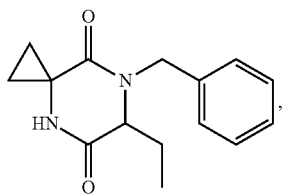 (I-b)

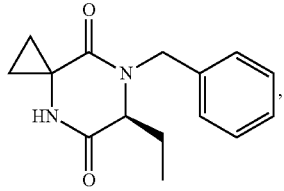 (I-c)

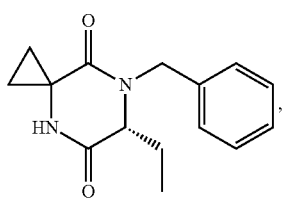 (I-d)

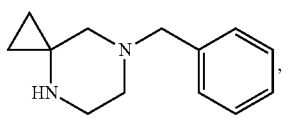 (I-bis-a)

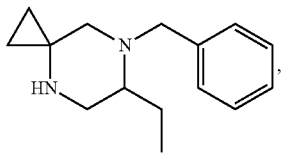 (I-bis-b)

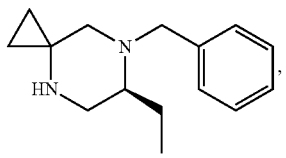 (I-bis-c)

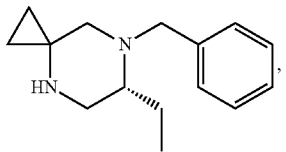 (I-bis-d)

Therefore, the compound of formula (II), (III), (V), (X):

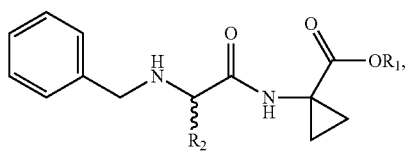 (II)

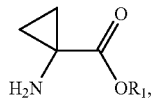 (III)

-continued

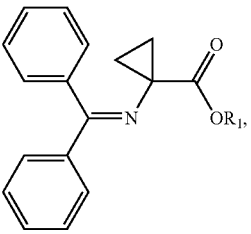 (V)

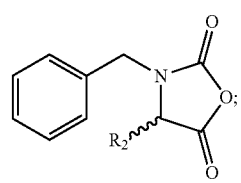 (X)

wherein in the compound of formula (II) $R_2$ is hydrogen, methyl or ethyl, and wherein in each of the compound $R_1$ is $C_{1-4}$ linear or branched alkyl; can be used for the for the preparations of compound of formula (VIII) or R or S optical isomer, or salt thereof:

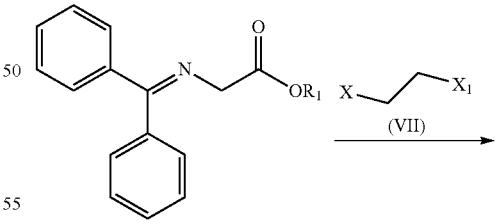 (VIII)

wherein $R_2$ is hydrogen, methyl or ethyl.

According to a preferred embodiment, the process mentioned can also be summarize by the following Schema 2:

Schema 2

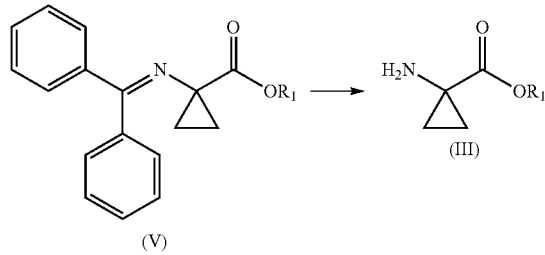

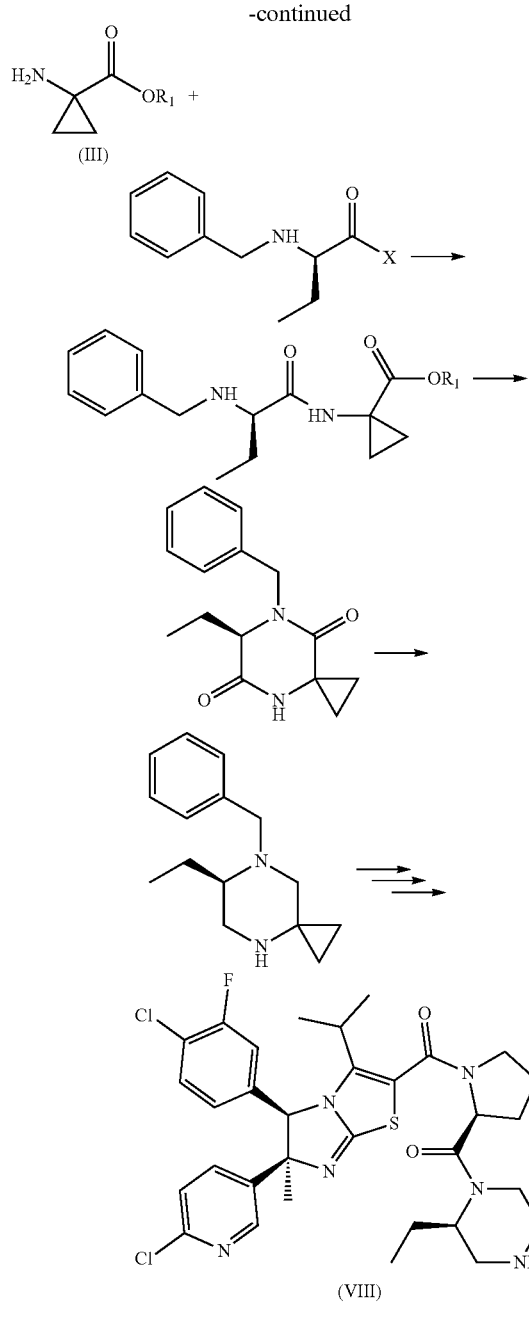

Thus, according to a preferred embodiment, the compound of formula (II) having the formula:

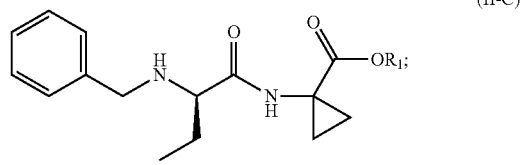

wherein $R_1$ is $C_{1-4}$ linear or branched alkyl;
can be used for the preparations of compound of formula (VIII) wherein $R_2$ is ethyl an is in R optical configuration.

The compounds of formula (I), (I-bis), (II), (IV) and (VIII) comprise either the R enantiomer, or the S enantiomer, or the racemic mixture or their mixtures in any R/S ratio.

The compound of formula (I), (I-bis), (II), (IV) and (VIII) having R configuration is a preferred compound.

The configurations above described always refers to the configuration of the carbon bonded to the $R_2$ group.

The compounds of formula (I) or of formula (I-bis) wherein $R_2$ is hydrogen methyl or ethyl are preferred since they are those involved in the preparation of marketed active pharmaceutical ingredients (API).

All the features and preferred embodiments of the process of the present invention given above can be combined in each possible combination to carry out the claimed process.

All of the intermediates and compounds of the present invention in particular those of formula (V), (III), (IV), (II), (I), (I-bis) can be in isolated or in not isolated form, from the reaction mixture wherein they are prepared.

According to the preferred embodiment, all of the intermediates and compounds isolated are typically in form of a solid or of an isolated oil.

According to the preferred embodiment, all of the intermediates and compounds not isolated are typically in form of solution with an organic solvent or water.

In an alternative embodiment, the compound of formula (II) can be synthetized according to the following Schema 3:

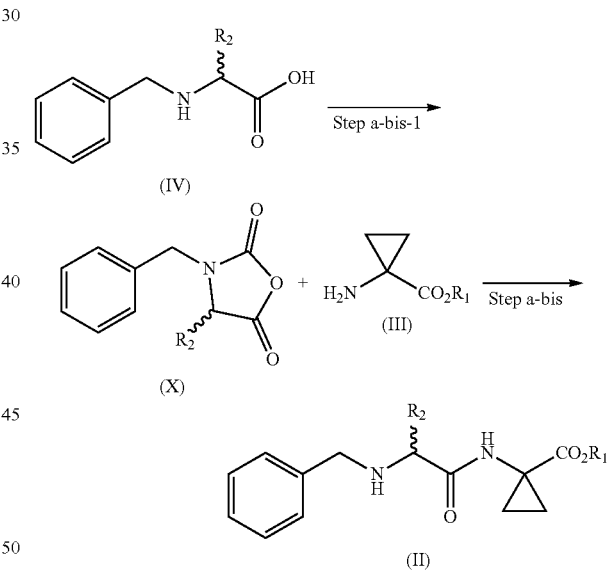

wherein $R_2$ is hydrogen, methyl or ethyl, and wherein $R_1$ is $C_{1-4}$ linear or branched alkyl;

The compound of formula (II) as well as the compound of formula (X) comprises either the single R enantiomer, or the S enantiomer, or the racemic mixture or their mixtures in any R/S ratio.

The compound of formula (II) as well as the compound of formula (X) having R configuration is a preferred compound.

The configurations above described always refers to the configuration of the carbon bonded to the $R_2$ group.

The step a-bis-1 of the process of the present invention can be carried out in presence of one or more basis.

In particular, the process is carried out in presence of an inorganic or an organic base or a mixture of these.

According to a preferred embodiment, the step a-bis-1 of the process according to the invention can be carried out in the presence of a base such as an organic base.

The inorganic base that can be used to carry out the step a-bis-1 of process of the present invention can be chosen among, for example, acetates, bicarbonates, carbonates, hydroxides, phosphates, alcoholates of alkaline or alkaline-heart metals.

Said inorganic base can also be sodium hydroxide, sodium carbonate, sodium bicarbonate, potassium hydroxide, potassium carbonate, potassium bicarbonate, caesium hydroxide, caesium carbonate, lithium hydroxide, lithium carbonate, potassium dihydrogen phosphate, potassium hydrogen phosphate, potassium phosphate, sodium dihydrogen phosphate, sodium hydrogen phosphate or sodium phosphate.

The step a-bis-1 of process according to the invention can be carried out in the presence of an organic base such as for example an organic amine of general formula $NR_3$ with R being linear or branched $C_{1-7}$ alkyl and wherein the three R groups can be the same or different. The amine can also be selected among pyrrolidine, N-alkyl substituted pirrolydine, piperidine, morpholine, N-alkyl substituted piperidine and N-alkyl substituted morpholine. Suitable bases are, for instance, N-Methylmorpholine, Triethylamine, diazabicyclooctane (DABCO), Ethyldiisopoprilamine and TMEDA (Tetramethylethylendiamine). The Triethylamine is preferred since it provides higher molar yields.

The step a-bis-1 of the process according to the invention can be carried out in the presence of one or more organic solvents such as, for example, toluene, xylene, halogenated solvents, dichloromethane (abbreviated DCM), dimethylformamide (DMF), N-methylporrolidone (NMP), dimethylsolphoxide (DMSO), tetrahydrofuran (THF), dioxane, methyl-t-butyl ether (MTBE), diethyl ether, acetate such as, for example, ethylacetate, methylacetate, propylacetate, isobutylacetate, isopropylacetate. Preferably the reaction is carried out in acetate solvent such as ethylacetate (abbreviate EcOAc), methylacetate, isopropylacetatetoluene, being more preferred EtOAc.

The step a-bis-1 is carried out in an organic solvent, preferably in EtOAc.

The step a-bis-1 can also be carried out with the compound of formula (IV), using, for example, a condensing agent such as a carbodiimide, like, for example, dicyclohexylcarbodiimide, or by means of phosgenation agent.

The phosgenation agent can be chosen between phosgene, dichloromethylcloroformate (Diphosgene), triphosgene, Carbonyldiimidazole, etc.

The step a-bis-1 is carried out using, for example, a condensing agent, preferably with phosgenation agent, more preferably with triphosgene.

The step a-bis of the process of the present invention is carried out in presence of one or more basis.

In particular, the process is carried out in presence of an inorganic or an organic base or a mixture of these.

According to a preferred embodiment, the step a-bis of the process according to the invention can be carried out in the presence of a base such as an inorganic base.

The inorganic base that can be used to carry out the step a-bis of process of the present invention can be chosen among, for example, acetates, bicarbonates, carbonates, hydroxides, phosphates, alcoholates of alkaline or alkaline-heart metals.

Said inorganic base can also be sodium hydroxide, sodium carbonate, sodium bicarbonate, potassium hydroxide, potassium carbonate, potassium bicarbonate, caesium hydroxide, caesium carbonate, lithium hydroxide, lithium carbonate, potassium dihydrogen phosphate, potassium hydrogen phosphate, potassium phosphate, sodium dihydrogen phosphate, sodium hydrogen phosphate or sodium phosphate.

The step a-bis of process according to the invention can be carried out in the presence of an organic base such as for example an organic amine of general formula $NR_3$ with R being linear or branched $C_{1-7}$ alkyl and wherein the three R groups can be the same or different. The amine can also be selected among pyrrolidine, N-alkyl substituted pirrolydine, piperidine, morpholine, N-alkyl substituted piperidine and N-alkyl substituted morpholine. Suitable bases are, for instance, N-Methylmorpholine, Triethylamine, diazabicyclooctane (DABCO), Ethyldiisoproprilamine and TMEDA (Tetramethylethylendiamine). The Triethylamine is preferred since it provides higher molar yields.

The step a-bis of the process according to the invention can be carried out in the presence of one or more organic solvents such as, for example, toluene, xylene, halogenated solvents, dichloromethane (abbreviated DCM), dimethylformamide (DMF), N-methylporrolidone (NMP), dimethylsolphoxide (DMSO), tetrahydrofuran (THF), dioxane, methyl-t-butyl ether (MTBE), diethyl ether. Preferably the reaction is carried out in aromatic solvent or an ether solvent such as toluene, xylene, MTBE, DCM, dioxane, methyl-tetrahydrofuran (Me-THF), THF, being more preferred THF and DCM.

The step a-bis is carried out in an organic solvent, preferably in THF or Me-THF or DCM or toluene mixtures thereof.

The step a-bis wherein in the compound of formula (IV) can be conveniently carried out in a solvent being DCM or THF or toluene.

The step a-bis wherein in the compound of formula (IV) can be conveniently carried out in DCM and trimethylamine, as base.

The step a-bis of the process according to the invention can be followed by the step b), previously described, for carrying out the cyclisation of the compound of formula (II) to the compound of formula (I).

EXPERIMENTAL SECTION

The starting material DPMGE, dibromoethane and N-benzyl glycine, are reactants largely commercially available, for example, for supplied by Sigma-Aldrich.

Volumes means volume of solvent per unit of product, thus, for example, 1 volume is 1 Liter per 1 Kilo, or 1 mL for 1 gram, or 1 microliter per 1 milligram. Thus, 10 volumes means for example 10 liters per 1 Kilogram of substance.

Example 1: Synthesis of the Compound of Formula (V) in which $R_1$ is Ethyl

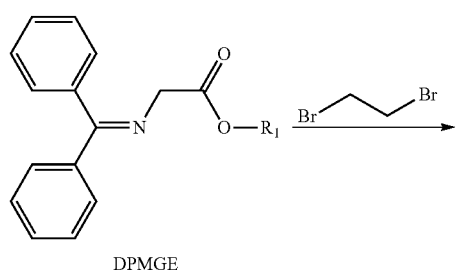

DPMGE

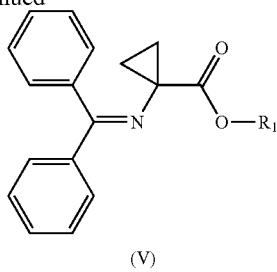

(V)

To a mixture of DPMGE (40 g, 150 mmol), KOH (41.9 g, 750 mmol), K₂CO₃ (41.4 g, 300 mmol), CsCO₃ (7.32 g, 22.5 mmol), TEBAC (6.82 g, 30 mmol) in methylisobuthyl ketone (250 ml) was added in around 40 min. a solution of 1,2-dibromoethane (33.76 g, 180 mmol) at 0° C. and the reaction was stirred at the same temperature for 16 hours. The obtained reaction mixture was filter and the filtrate containing the compound (V) was used directly in the next step.

Example 2: Synthesis of the Compound of Formula (III) in which R₁ is Ethyl

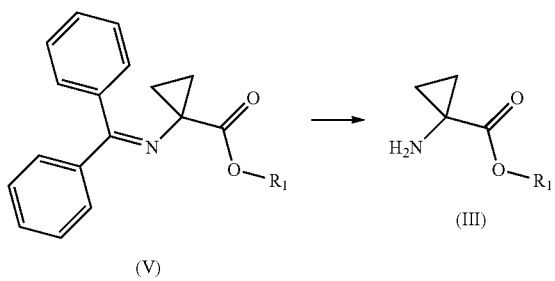

To a mixture of the organic solution obtained in the Example 1 and water (200 ml) and was added a solution of 1M HCl until the pH is 3. The reaction mixture was stirred at room temperature until the reaction was complete (the compound (V) was disappearing, IPC by TLC ethyl acetate:petroleum ether=1:3). Then, the reaction mixture was extract with MIBK (100 mL) for three times. To the obtained aqueous mixture was added DCM (200 mL) and the pH was brought to 9 by adding a solution of 10% NaOH. Then, the obtained mixture was extracted with DCM (100 mL) for three times. The combined organic layer was concentrate on vacuum to give product (III) (8.7 g, 45% overall yield of 2 steps) as a pale yellow oil.

Example 3: Synthesis of the Compound of Formula (V) in which R₁ is Ethyl

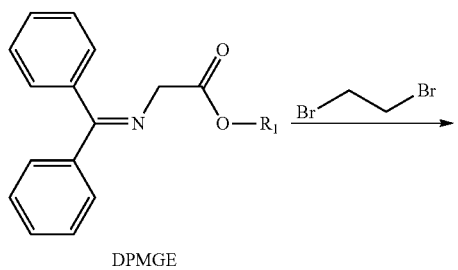

DPMGE

To a solution of DPMGE (350 g, 1.31 mol) in toluene (1 L) was added in around 40 min. a suspension of sodium hydride (60% in mineral oil, 78.65 g, 1.95 mol) in toluene (750 mL). The mixture was heated at 110° C. and was stirred for 1 h. To the obtained reaction mixture was added 1,2-dibromoethane (738.4 g, 3.9 mol) and the reaction was stirred at the same temperature for 3 hours. To the obtained reaction mixture was added a suspension of sodium hydride (60% in mineral oil, 78.65 g, 1.95 mol) in toluene (750 mL). The mixture was stirred at 110° C. for 4 h. The obtained reaction mixture was cooled to 5-10° C. and was slowly dosed water (1.4 L). The obtained mixture was stirred for 1 hour at room temperature. The aqueous solution was spit-off and the obtaining organic solution containing the compound (V) was used directly in the next step. The GC purity according to the method of example 16 is 80-85%.

Example 4: Synthesis of the Compound of Formula (III) in which R₁ is Ethyl

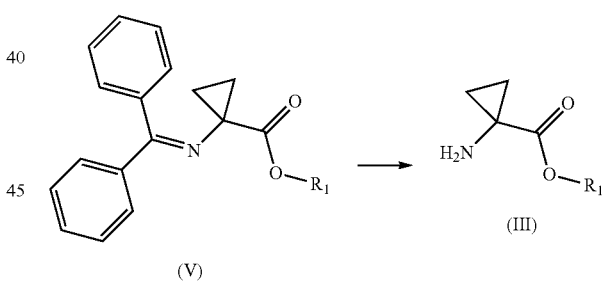

To the organic solution obtained in the Example 1 was added a solution of acetic acid (130 g, 2.16 mol) in water (5 L). The reaction mixture was heated a T=50° and was stirred for 10-13 hours or until the reaction was complete (the compound (V) was disappearing, IPC by TLC ethyl acetate:petroleum ether=1:3). Then, the reaction mixture was cooled to room temperature and the phase was spitted. The obtaining aqueous solution containing the compound (III) was used directly in the next step.

Alternatively, to the obtained aqueous mixture was added DCM (1 L) and the pH was brought to 9 by adding a solution of 10% NaOH. Then, the obtaining mixture was extracted with DCM (1 L) for three times. The combined organic layer was concentrate on vacuum to give product (III) (84.55 g, 50% overall yield of 2 steps) as a pale yellow oil.

Example 5: Synthesis of the Compound of Formula (IV) in which $R_2$ is Hydrogen and X is Chlorine

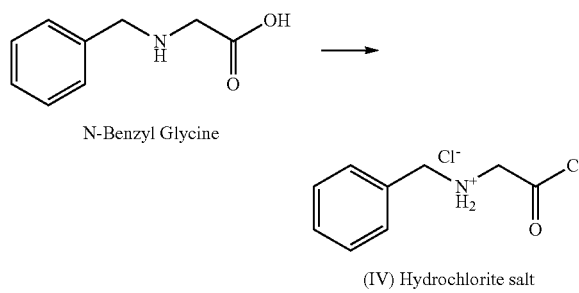

To a suspension of $PCl_5$ (1.51 g, 7.25 mmol) in Toluene (30 ml, 30 V) was added benzyl-glycine (1 g, 6.05 mmol). The reaction mixture was stirred at r.t. for 6 h. To the obtained reaction mixture was filtered and the obtained solid was washed with DCM (10 mL) for two times. The obtaining solid was dried on vacuum to give product (IV) hydrochloride salt (1.25 g, 93% yield) as a white solid.

Example 6: Synthesis of the Compound of Formula (II) in which $R_1$ is Ethyl and $R_2$ is Hydrogen

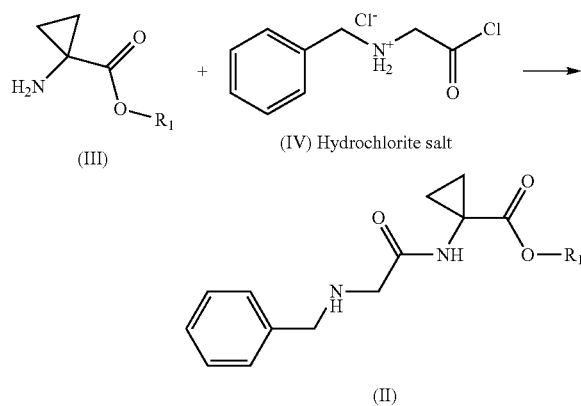

To a suspension of compound (IV) (0.16 g, 0.7 mmol) and compound (III) (wherein $R_1$ is ethyl, 0.1 g, 0.6 mmol) in DCM (2.50 ml) was added slowly TEA (0.21 g, 2 mmol). The reaction was stirred at r.t. for 3 hours, then the solvent was concentrated under reduced pressure. The residue obtained was diluted with ethyl acetate, washed with saturated aqueous sodium bicarbonate solution and saturated brine, and then dried over anhydrous sodium sulphate. The solvent was evaporated under reduced pressure and the residue obtained was purified by silica gel column chromatography to give the title compound (27 mg, 16%). 1H-NMR (500 MHz, DMSO-$d_6$): 1.00-1.03 (2H, m), 1.14 (3H, t, J=7 Hz), 1.33-1.36 (2H, m), 2.56 (1H, brs), 3.06 (2H, s), 3.68 (2H, s), 4.37 (2H, q, J=7 Hz), 7.23-7.32 (5H, m), 8.38 (1H, s). 13C-NMR (125 MHz, DMSO-$d_6$): 172.26; 172.02; 140.24; 128.07; 128.01; 126.60; 60.52; 52.34; 51.17; 40.00; 39.83; 39.76; 39.67; 39.50; 39.33; 39.16; 39.00; 32.58; 16.59; 14.00.

Example 7: Synthesis of the Compound of Formula (I) in which $R_2$ is Hydrogen

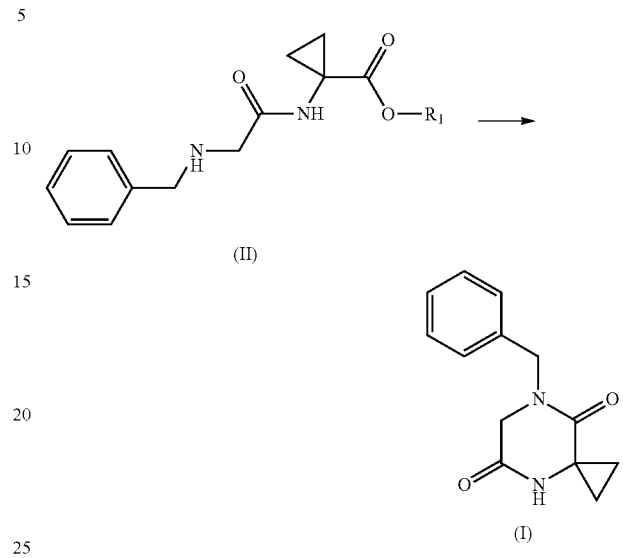

A solution of compound (II) (wherein $R_1$ is ethyle) (1.2 kg, 4.34 mol) in n-Butanol (4.8 L, 4V) was heated at T of reflux and stirred for 10 h. Then, the reaction mixture was cooled slowly to T=5-10° C. and stirred at this temperature for 1 h. The obtaining suspension was filtered and the obtaining solid was washed with n-heptane (300 mL) for three times. To the obtained cake was added a solution of HCl (35%, 10.7 g) in water (3.7 kg, 3V) and the obtaining mixture was stirred at r.t. for 2 h. Then, the mixture was cooled to 5-10° C. and stirred for 1 h. The obtaining suspension was filtered and washed with water (400 mL) for three times. The obtaining solid was dried on vacuum to give crude product (I) (770 g, GC purity 98.9%, HPLC purity 99.2%) as a white solid.

The obtained crude product (I) was recrystallized from a mixture of acetonitrile (7.11 kg) and acetic acid (38.5 g), the obtaining suspension was heated at temperature of reflux to giave a clear pale yellow solution. Then, the solution was cooled to 5-10° C. and stirred for 1 h. The obtaining suspension was filtered and washed with acetonitrile (100 mL) for three times. The obtaining solid was dried on vacuum to give product (I) (690 g, 69% yield and 97% yield of the recrystallization, HPLC purity 99.84%, max single impurity 0.07%; GC purity 99.86%, max single impurity 0.04%) as a white solid.

Example 8: Synthesis of the Methyl Ester of the Compound of Formula (IV) in which $R_2$ is Ethyl in R Configuration (Compound (IV-a))

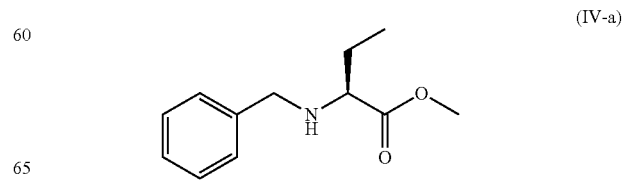

The compound of formula (IV-a) was synthesized according to the teaching of Tethahedron 57(2001), 6589-6605.

Example 9: Synthesis of the Compound of Formula (IV) in which R₂ is Ethyl in R Configuration (Compound (IV-b))

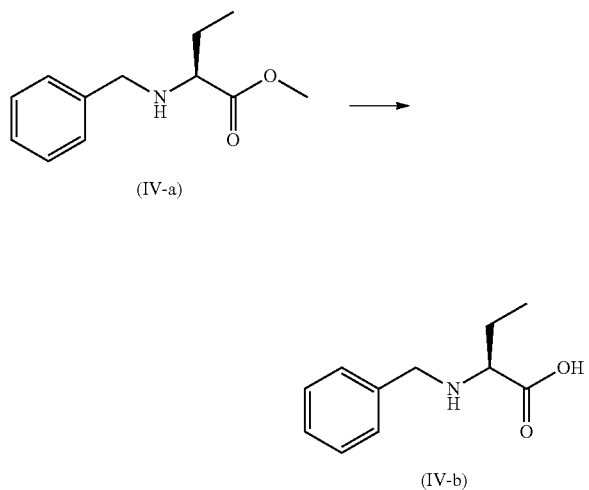

A solution of compound (IV-a) (1 g, 4.82 mmol) was dissolved in a mixture of aq HCl (5 mL, 20%) and dioxane (5 mL) and stirred for 3 days at 60° C. Evaporation of the solvent in vacuo gave compound (IV-b) (922 mg, 99% yield).

Example 10: Synthesis of the Compound of Formula (I) in which R₂ is Ethyl (Intermediate 3)

Intermediate 3

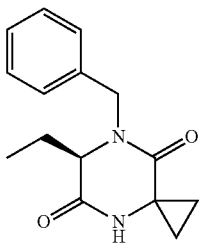

The Intermediate 3 was synthesized according to the procedures given from example 5 to example 7, starting from (R)-2-benzylamino-butanoic acid (compound (IV-b)) obtained in the Example 9. The product intermediate 3 has been characterized by NMR. 1H-NMR (400 MHz, DMSO-d6): 0.93-0.98 (2H, m), 0.99 (3H, t, J=7.6 Hz), 1.35-1.40 (1H, m), 1.80-1.86 (1H m), 1.91-1.98 (2H, m), 3.89 (1H, t, J=5.2 Hz), 3.94 (1H, d, J=14.9 Hz), 5.35 (1H, d, J=14.9 Hz), 7.25-7.35 (5H, m), 7.51 (1H, brs). MS (ESI) m/z: 259 [(M+1)⁺].

Example 11: Synthesis of the Compound of Formula

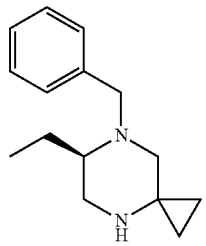 [SMILES: CC[C@@H]1CNC2(CC2)CN1Cc1ccccc1]

A solution of borane-tetrahydrofuran complex in THF (0.93 M, 375 ml, 350 mmol) was added to a THF (200 ml) solution of the Intermediate 3 (22.42 g, 86.8 mmol) prepared in example 10 under ice cooling and then the resulting mixture was heated to reflux for 19 hours. Methanol (130 ml) was added to the reaction mixture under ice cooling, the resulting mixture was stirred for 60 minutes and then the solvent was concentrated under reduced pressure. Ethanol (400 ml), water (100 ml), and triethylamine (150 ml) were added to the residue obtained, the resulting mixture was heated to reflux for 2 hours and then the solvent was concentrated under reduced pressure. The residue obtained was diluted with ethyl acetate, washed with saturated aqueous sodium bicarbonate solution and saturated brine, and then dried over anhydrous sodium sulphate. The solvent was evaporated under reduced pressure and the residue obtained was purified by silica gel column chromatography [chloroform:methanol=10:1 (v/v)] to give the title compound (11.20 g, 59%).

Example 12: Synthesis of the Compound (6R)-7-benzyl-6-ethyl-4-(trifluaraacetyl)-4,7-ciiazaspira [2.5]actane, of Formula

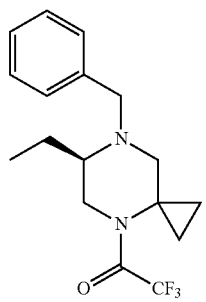 [SMILES: CC[C@@H]1CN(C(=O)C(F)(F)F)C2(CC2)CN1Cc1ccccc1]

Trifluoroacetic anhydride (8.35 ml, 60 mmol) was added dropwise to a dichloromethane (200 ml) solution of the compound obtained in the example 11 (11.20 g, 50 mmol) and triethylamine (16.7 ml, 120 mmol) under ice cooling and the resulting mixture was stirred at the same temperature for 1 hour. Saturated aqueous sodium bicarbonate solution was added to the reaction mixture and the resulting mixture was diluted with chloroform, then washed with saturated brine, and dried aver anhydrous sodium sulphate. The solvent was evaporated under reduced pressure to give the title compound (16.15 g, 99%) as a colourless oil. 1H-NMR (400 MHz, DMSO-d₆): 0.65-0.70 (1H, m), 0.85-0.90 (2H, m), 0.91 (3H, t, J=7.4 Hz), 1.18-1.23 (1H, m), 1.46-1.53 (1H m), 1.66-1.75 (1H, m), 2.31-2.36 (1H, m), 2.38-2.45 (2H, m), 3.32 (1H, d, J=13.9 Hz), 3.40-3.47 (1H, m), 3.84 (1H, d, J=11.7 Hz), 3.97 (1H, d, J=13.9 Hz), 7.18-7.23 (1H, m), 7.27-7.31 (4H, m). MS (ESI) m/z: 327 [(M+H)⁺].

Example 13: Synthesis of the Compound (6R)-6-ethyl-4-(trifluaraacetyl)-4,7-ciiazaspira[2.5]actane hycirachlaricie, of Formula

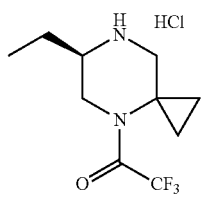 [SMILES: Cl ; CC[C@@H]1CN(C(=O)C(F)(F)F)C2(CC2)CN1]

A solution of 1 N hydrochloric acid in ethanol (100 ml, 100 mmol) and 5% palladium on carbon (3 g) were added to an ethanol (250 ml) solution of the compound (15 g, 46 mmol) obtained in Example 12 above and the resulting mixture was subjected to catalytic reduction for 15 hours in a hydrogen atmosphere. The catalyst was removed by filtration through celite and then the filtrate was concentrated under reduced pressure. An ethanol/diethyl ether mixed solvent was added to the residue obtained and the deposited solid was collected by filtration to give the title compound (10.67 g, 85%) as a colourless solid. 1H-NMR (400 MHz, DMSO-d₆): 0.89-0.94 (1H, m), 0.99 (3H, t, J=7.6 Hz), 1.16-1.21 (1H, m), 1.25-1.31 (1H, m), 1.41-1.48 (1H, m), 1.66-1.74 (1H, m), 1.77-1.85 (1H, m), 2.86 (1H, d, J=12.9 Hz), 3.24-3.32 (1H, m), 3.37-3.44 (1H, m), 3.45 (1H, d, J=12.9 Hz), 4.06-4.14 (1H, m). MS (ESI) m/z: 237 [(M+H)⁺].

Example 14: Synthesis of Intermediate 2 Named (6R)-6-ethyl-7-[(4R)-4-fluara-L-pralyl]-4-(trifluaraacetyl)-4,7-ciiazaspira[2.5]actane have Formula

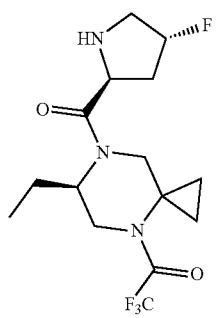

Intermediate 2

The compound was synthesized, starting from the compound obtained in example 13, according to the teaching of EP2380892B, reference example 11.

Example 15: Synthesis of the Compound of Formula (VIII) in which R₂ is R-Ethyl, i.e. Compound (IX)

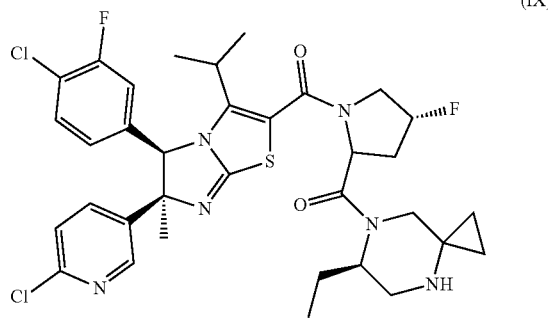

The compound was synthesized, starting from the compound obtained in example 14, according to the teaching of EP2380892B, Example 5 and Example 6.

Example 16: Synthesis of the Compound of Formula (II) in which R₁ is Ethyl and R₂ is Hydrogen, i.e. Compound (II-a)

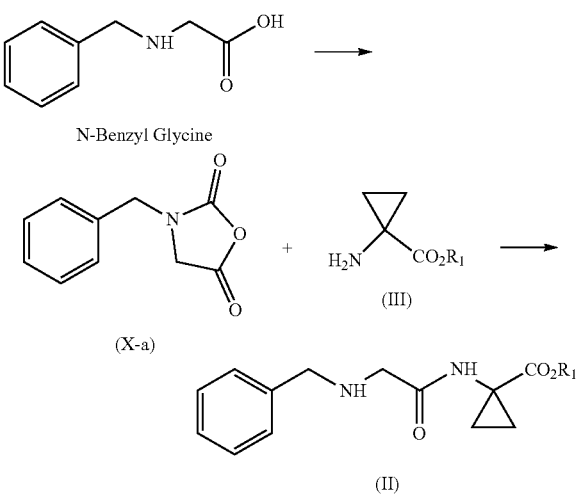

To a solution of triphosgene (3.6 g, 0.4 eq) in ethyl acetate (i.e. EtOAc) (200 ml, 40V) was added N-Benzyl glycine (5 g, 1 eq). Then a solution of triethylamine (3.37 g, 1.1 eq) in EtOAc (50 ml, 10V) was added dropwise over a period of 40 min, and the mixture was stirred for another 4 h. The obtained reaction mixture was filtered and concentrate under vacuum to give the compound of formula (X-a) 3.64 g, yield 63%, HPLC purity 96.43%. It was dissolved in CH₂Cl₂ (i.e. DCM) (25 ml, 5V), reserved.

In a 50 ml glass reactor, was charged compound (III) (wherein R1 is ethyl, 3.5 g, 0.7 eq), triethylamine (4.29 g, 1.4 eq) and CH₂Cl₂ (25 ml, 5V). the obtained solution was added dropwise to the DCM solution of compound of formula (X-a). After adding, the mixture was stirred for 7 h. Then water (50 ml, 10V) was charged and the phase was separated. The organic layer was extracted with 2N aqueous HCl (20 ml×2, 8V). The aqueous phase was adjusted to pH 8 with sodium bicarbonate. Then the obtained solution was extracted with DCM (25 ml×2, 10V). The aqueous phase was concentrated under reduced pressure to obtain compound (II) (in which $R_1$ is Ethyl) 2.17 g, yield 41.3%, GC purity 60%.

Example 17: Synthesis of the Compound of Formula (I) in which $R_2$ is Hydrogen

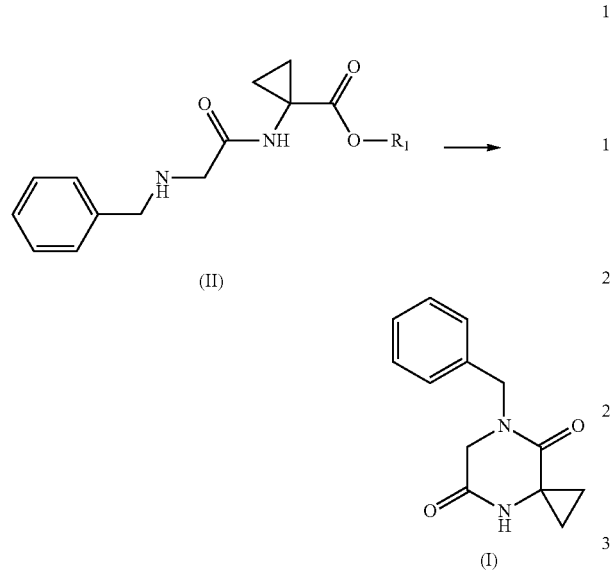

To a solution of compound (II) (wherein R1 is ethyle) (0.67 g, 1 eq) in butyl alcohol (3.3 ml, 5V) was added acetic acid (0.13 g, 20% weat). The mixture was refluxed for 10 h. After the reaction was complete, n-Hexane (5.4 ml, 8V) was added to the mixture. The obtained suspension was filtered and washed with n-Hexane (1.3 ml, 2V). The obtaining off-white solid was dried on vacuum to give product (I) 0.2 g, yield 36%, GC purity 98.44%.

Example 18: Synthesis of the Compound of Formula (IV) in which $R_2$ is Ethyl in R Configuration (Compound (IV-b))

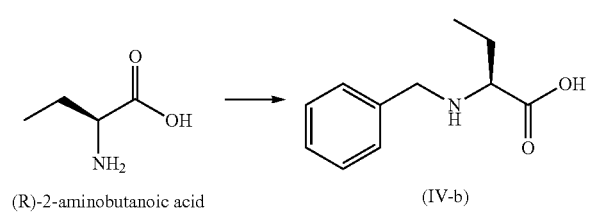

A mixture of (R)-2-aminobutanoic acid (5 g, 1 eq), aqueous sodium hydroxide solution (2 mol/L, 24 ml, 1 eq) and benzaldehyde (5.15 g, 1 eq) was stirred at 25° C. for 4 hour. Then the resulting mixture was cooled to 0° C., and to the mixture was added sodium borohydride (1.05 g, 0.57 eq) in portions. After the addition, the resulted mixture was stirred at 25° C. for 12 hours. After the reaction was finished, the reaction mixture was extracted with DCM (10 ml×3). The organic phases were discarded. The water phase was adjusted to pH 5-6 with concentrated hydrochloric acid, then the mixture was filtrated to give the product as a white solid 5.8 g, yield 62%, HPLC purity 98.33%, [α]Dr.t.=−14.6 (c=0.4 g/100 ml, $H_2O$).

Example 19: Synthesis of the Compound of Formula (II) in which $R_1$ is Ethyl and $R_2$ is Ethyl in R Configuration (Compound (II-c))

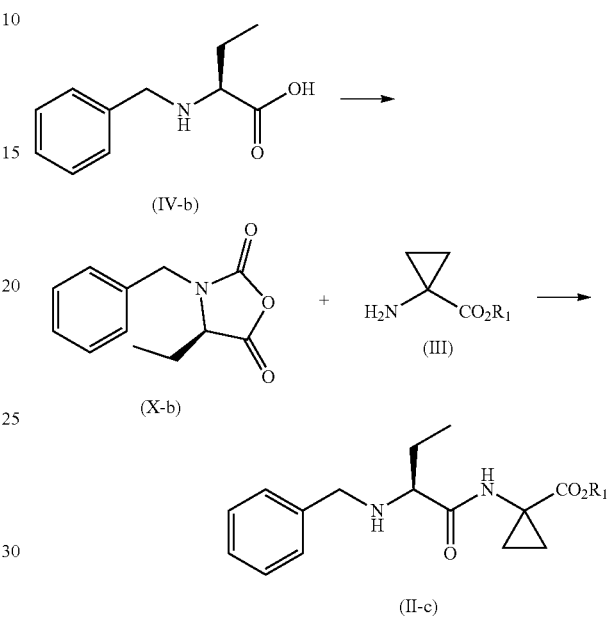

To a solution of triphosgene (1.96 g, 0.4 eq) in EtOAc (128 ml, 40V) was added the R-2-ethyl-N-Bn glycine (compound IV-b, 3.2 g, 1 eq). Than a mixture of Triethylamine (1.84 g, 1.1 eq) in EtOAc (32 ml, 10V) was added dropwise to the solution over a period of 40 min, and the mixture was stirred for another 4 h. The reaction mixture was filtered and evaporated to give the compound of formula (X-b) 2.54 g, yield 70%, HPLC purity 93.6%. It was dissolved in DCM (16 ml, 5V).

To a 50 ml glass reactor, added amino ester hydrochloride (1.92 g, 0.7 eq), Triethylamine (2.35 g, 1.4 eq) and DCM (16 ml, 5V). Filtered and filtrate was added dropwise to the solution of compound of formula (X-b). After adding, the mixture was stirred for another 7 h. water (32 ml, 10V) was charged and separated. The organic layer was extracted with 2N HCl aq (12.8 ml×2). The aqueous phase was adjusted to pH 8 with sodium bicarbonate. The solution was extracted with DCM (16 ml×2) and concentrated under reduced pressure to obtain compound (II-c) 1.58 g, yield 45%, GC purity 62%. The structure was confirmed by GC-MS.

Example 20: Synthesis of the Compound of Formula (I) in which $R_2$ is Ethyl (Intermediate 3)

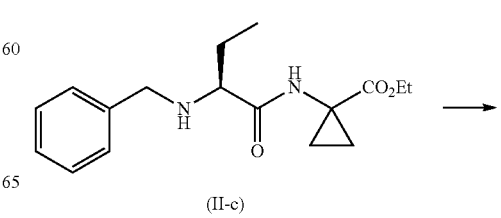

-continued

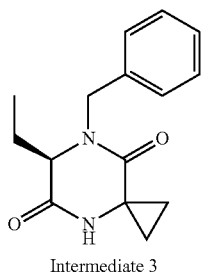

Intermediate 3

To a solution of compound (II-c) (0.7 g, 1 eq) in butyl alcohol (3.5 ml, 5V) was added acetic acid (0.14 g, 20% wt). The mixture was refluxed for 10 h. After the reaction was complete, the reaction solution was concentrated under reduced pressure. The residue was chromatographed (EtOAc:n-Hexane=1:2) to get the intermediate 3 as a yellow oil 0.25 g, yield 42.4%, GC purity 98.42%. [α]Dr.t.=−63 (c=0.4 g/100 ml, CH$_3$OH).

Example 21: Synthesis of the Compound of Formula (IV) in which R2 is Methyl in R Configuration (Compound (IV-c))

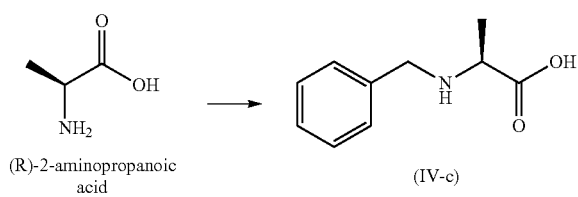

(R)-2-aminopropanoic acid　　　　　　　(IV-c)

A mixture of (R)-2-aminopropanoic acid (5 g, 1 eq) in aqueous sodium hydroxide (2 mol/L, 28 ml, 1 eq) and benzaldehyde (6 g, 1 eq) was stirred at 25° C. for 4 hour. Then the mixture was cooled to 0° C., and to the mixture was added sodium borohydride (1.21 g, 0.57 eq) in portions. After the addition, the resulted mixture was stirred at 25° C. for 12 hours. After the reaction was finished, the reaction mixture was extracted with DCM (10 ml×3). The organic phases were discarded and the water phase was adjusted to pH 5-6 with concentrated hydrochloric acid, then the mixture was filtrated to give the compound (II-c) as a white solid 4.27 g, yield 42.5%, HPLC purity 99.12%, [α]Dr.t.=−15 (c=0.4 g/100 ml, H$_2$O).

Example 22: Synthesis of the Compound of Formula (II) in which R$_1$ is Methyl and R$_2$ is Ethyl in R Configuration

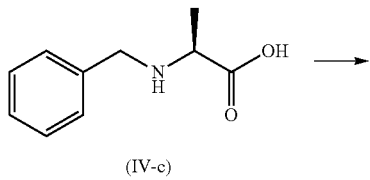

(IV-c)

-continued

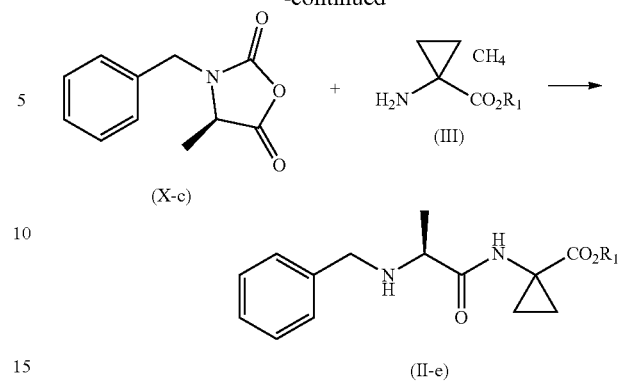

(X-c)

(II-e)

To a solution of triphosgene (3.15 g, 0.4 eq) in EtOAc (190 ml, 40V) was added the compound (IV-c) (4.75 g, 1 eq), Triethylamine (2.95 g, 1.1 eq) in EtOAc (47.5 ml, 10V) was added dropwise to the solution over a period of 40 min, and the mixture was stirred for another 4 h. The reaction mixture was filtered and evaporated to give the compound of formula (X-c) 3.26 g, yield 60%, HPLC purity 89.34%. It was dissolved in DCM (23.4 ml, 5V), reserved.

To a 50 ml glass reactor, added compound (III) hydrochloride (3.07 g, 0.7 eq), Triethylamine (3.75 g, 1.4 eq) and DCM (23.4 ml, 5V). Filtered and filtrate was added dropwise to the solution of compound of formula (X-c). After adding, the mixture was stirred for another 7 h. Water (47.5 ml, 10V) was charged and the phase was separated. The organic layer was extracted with 2N HCl aq (19 ml×2). The obtaining aqueous phase was adjusted to pH 8 with sodium bicarbonate and the solution was extracted with DCM (23.4 ml×2). The obtained aqueous phase was concentrated under reduced pressure to obtain compound (II) (in which R$_1$ is Methyl and R$_2$ is Ethyl in R configuration) 2.05 g, yield 44.4%, GC purity 80.3%.

Example 23: Synthesis of the Compound of Formula (I) in which R$_2$ is Methyl

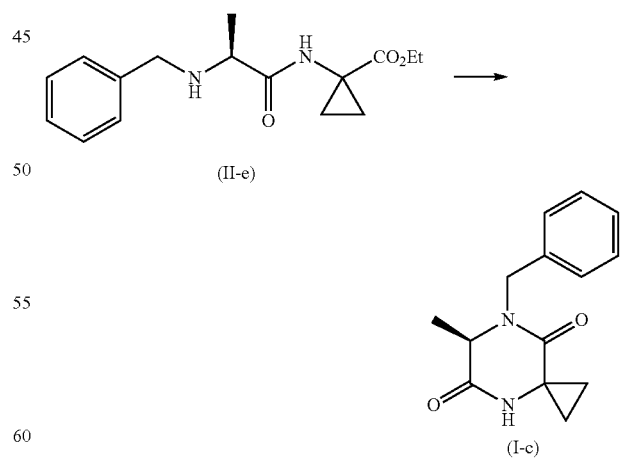

(II-e)

(I-c)

To a solution of compound obtained in the example 22 (2.05 g, 1 eq) in butyl alcohol (10.25 ml, 5V) was added acetic acid (0.41 g, 20% wt). The mixture was refluxed for 10 h. After the reaction was complete, the reaction solution was concentrated under reduced pressure. The residue was chromatographed (EtOAc:n-Hexane=1:2) to get the product as a yellow oil 1.07 g, yield 62.2%, GC purity 88.8%. [α]Dr.t.=−27.3 (c=0.4 g/100 ml, CH₃OH).

Example 24: Analytic Method for Determining the Chemical Purity and the Amount of Impurities of the Present Invention Method A: method for monitoring the reaction of example from 1 to 5, via the following HPLC method:

| Column | Intersil ODS-3 150 * 4.0 mm, 3 µm |  |  |
|---|---|---|---|
| Temp. Column | 30° C. |  |  |
| Mobile Phase A | 1.0 g potassium dihydrogen phosphate in 1000 mL water, adjust pH to 7.0 with NaOH |  |  |
| Mobile Phase B | Acetonitrile |  |  |
|  | Time (min) | % A | % B |
| Gradient | 0.01 | 95.0 | 5.0 |
|  | 15.00 | 50.0 | 50.0 |
|  | 25.00 | 10.0 | 90.0 |
|  | 30.00 | 10.0 | 90.0 |
|  | 30.01 | 95.0 | 5.0 |
|  | 35.00 | 95.0 | 5.0 |
| Run Time | 35.0 min |  |  |
| Flow | 1.0 mL/min |  |  |
| UV Detector | 210 nm (main)/254 nm |  |  |
| Injection Volume | 5 µL |  |  |
| Analysis Time | 30.0 min |  |  |
| Diluent | Acetonitrile |  |  |

Method B: method for monitoring the reaction of example 6 and 7 and the purity of the compound of formula (I) wherein $R_2$ is hydrogen, via the following HPLC method:

| Column | XBridge Shield RP18 (250 * 4.6 mm, 5 µm) |  |  |
|---|---|---|---|
| Temp. Column | 20° C |  |  |
| Mobile Phase A | 1.0 g Ammonium dihydrogen phosphate and 5 ml Ammonium hydroxide in 1000 mL water, adjust pH to 7.0 with sodium hydroxide |  |  |
| Mobile Phase B | Acetonitrile |  |  |
|  | Time (min) | % A | % B |
| Gradient | 0.01 | 90.0 | 10.0 |
|  | 15.00 | 90.0 | 10.0 |
|  | 35.00 | 25.0 | 75.0 |
|  | 40.00 | 25.0 | 75.0 |
|  | 45.00 | 90.0 | 10.0 |
|  | 50.00 | 90.0 | 10.0 |
| Run Time | 50.0 min |  |  |
| Flow | 1.0 mL/min |  |  |
| UV Detector | 210 nm (main)/254 nm |  |  |
| Injection Volume | 5 µL |  |  |
| Analysis Time | 50.0 min |  |  |
| Diluent | Acetonitrile |  |  |

Method C: method for monitoring the reaction of example 6 and 7 and the purity of the compound of formula (I) wherein $R_2$ is hydrogen, via the following GC method:

| Column | HP-5 30 m × 320 µm × 0.25 µm |
|---|---|
| Front Inlet | Heater 250° C. |
|  | Entry Pressure 7.3234 psi |
|  | Total Flow 19.5 ml/min |
|  | Septum Purge 3 ml/min |

-continued

| Carrier Gas | Nitrogen |  |  |
|---|---|---|---|
| Mode | Split, Split Ratio: 10:1 |  |  |
| Column Flow | 1.5 ml/min |  |  |
| Injection volume | 0.2 ul |  |  |
| | Rate (° C./min) | Value (° C./min) | Hold Time (° C./min) | Run Time (° C./min) |
| Oven |  | 60 | 0 | 0 |
|  | 10 | 300 | 5 | 29 |
| Detection | Flame ionization |  |  |
| Heater | 300° C. |  |  |
| H2 Flow rate | 30 ml/min |  |  |
| Air Flow rate | 300 ml/min |  |  |
| Make up (N2) | 25 ml/min |  |  |

The invention claimed is:

1. A process for the preparation of the compound of formula (I) or R or S optical isomer:

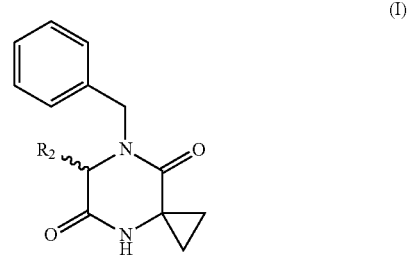

(I)

wherein $R_2$ is hydrogen, methyl or ethyl, comprising the following steps (a) and (b), or step (a-bis) and (b):

(a) reacting of the compound of formula (III):

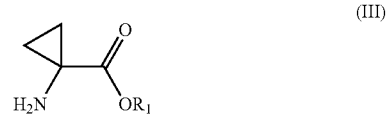

(III)

wherein $R_1$ is $C_{1-4}$ linear or branched alkyl, with a compound of formula (IV):

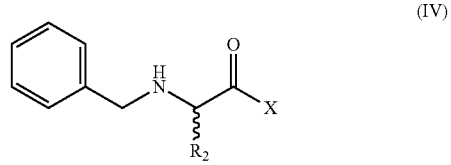

(IV)

wherein $R_2$ is hydrogen, methyl or ethyl, and wherein X is chosen between hydroxyl, halogen or any group used to activate the carboxyl function;

for providing the compound of formula (II) or salt thereof:

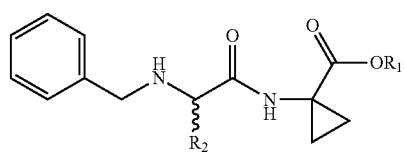

(II)

wherein $R_2$ is hydrogen, methyl or ethyl, and wherein $R_1$ is $C_{1-4}$ linear or branched alkyl;
or
(a-bis) reacting of the compound of formula (III):

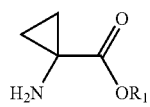

(III)

wherein $R_1$ is $C_{1-4}$ linear or branched alkyl,
with a compound of formula (X):

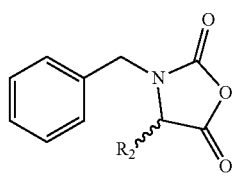

(X)

wherein $R_2$ is hydrogen, methyl or ethyl;
for providing the compound of formula (II) or salt thereof:

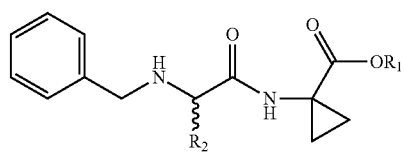

(II)

wherein $R_2$ is hydrogen, methyl or ethyl, and wherein $R_1$ is $C_{1-4}$ linear or branched alkyl;
(b) cyclizing the compound of formula (II) obtained in step (a) or (a-bis) to give the compound of formula (I):

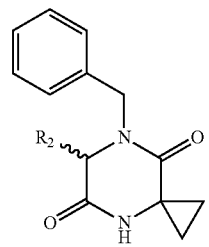

(I)

wherein $R_2$ is hydrogen, methyl or ethyl.

2. The process according to claim 1, comprising the previous steps for preparing of the compound of formula (III):

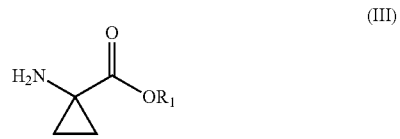

(III)

wherein $R_1$ is $C_{1-4}$ linear or branched alkyl,
said previous steps being the following steps:
a-1) reacting the compound of formula (VI):

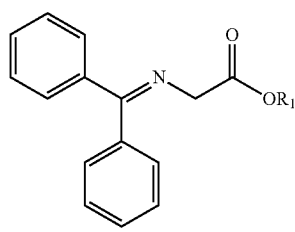

(VI)

wherein $R_1$ is $C_{1-4}$ linear or branched alkyl,
with a compound of formula (VII):

(VII)

wherein $X_1$ and $X_2$ are independently an halogen, mesilate, tosilate, besilate or triflate;
to give the compound of formula (V):

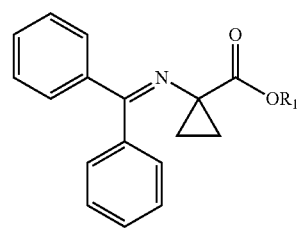

(V)

wherein $R_1$ is $C_{1-4}$ linear or branched alkyl;
b-1) deprotecting the compound of formula (V):

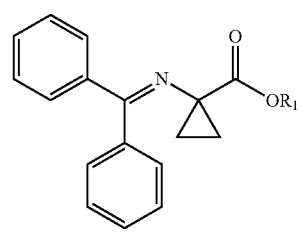

(V)

obtained in step a-1) to give the compound of formula (III):

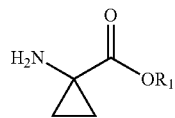
(III)

wherein $R_1$ is $C_{1-4}$ linear or branched alkyl.

3. The process according to claim 1, comprising the further step of reducing the compound obtained in step (b), of formula (I):

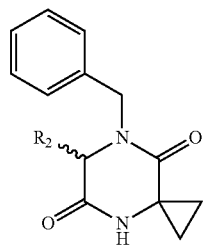
(I)

wherein $R_2$ is hydrogen, methyl or ethyl, to give the compound of formula (I-bis) or salt thereof:

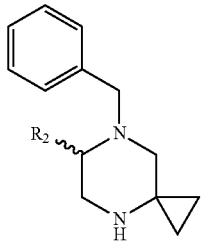
(I-bis)

wherein $R_2$ is hydrogen, methyl or ethyl.

4. The process according to claim 1, wherein $R_2$ of the compounds of formula (I), (I-bis), (II) and (IV) is hydrogen.

5. The process according to claim 1, wherein $R_1$ of the compound of formula (II), (III), (V) and (VI) is ethyl.

6. The process according to claim 2, wherein $X_1$ and $X_2$ of the compound of formula (VII) are both bromine.

7. The process according to claim 2, wherein the process in the step a-1) is carried out by means of sodium hydride or sodium hydride 60% in mineral oil.

8. The process according to claim 7, wherein the process is carried out in an organic solvent being toluene.

9. The process according to claim 2, in which the process in the step b-1) is carried out in n-butanol.

10. The process according to claim 2, in which the process in the step b-1) is carried out in presence of acetic acid.

11. The process according to claim 1, wherein the compound of formula (I), in which $R_2$ is hydrogen, obtaining at the end of step b-1), is purified by crystallization or recrystallization from acetonitrile or a mixture of acetonitrile and acetic acid.

* * * * *